United States Patent [19]

Steiner et al.

[11] 4,376,773

[45] Mar. 15, 1983

[54] 10-SUBSTITUTED 5-CYANOMETHYLENE-10,11-DIHYDRO-DIBENZO-[A,D]-CYCLOHEPTENES, THEIR PREPARATION, AND THERAPEUTIC AGENTS CONTAINING THESE COMPOUNDS

[75] Inventors: Gerd Steiner, Kirchheim; Hans P. Hofmann, Ludwigshafen; Horst Kreiskott, Wachenheim; Hans-Juergen Teschendorf, Ludwigshafen, all of Fed. Rep. of Germany

[73] Assignee: BASF Aktiengesellschaft, Fed. Rep. of Germany

[21] Appl. No.: 237,964

[22] Filed: Feb. 25, 1981

[30] Foreign Application Priority Data

Mar. 8, 1980 [DE] Fed. Rep. of Germany ....... 3009045

[51] Int. Cl.³ .............. A61K 31/495; A61K 31/445; A61K 31/55; C07D 241/04
[52] U.S. Cl. .................................. 424/251; 424/250; 544/154; 544/381; 546/246; 260/239 R; 260/239 B; 260/239 BC; 548/529
[58] Field of Search .......................... 544/381, 154; 260/239 B, 239 BC, 239 R; 424/250, 251; 546/246

[56] References Cited

U.S. PATENT DOCUMENTS

| | | | |
|---|---|---|---|
| 3,325,497 | 6/1967 | Fouche | 544/381 |
| 3,459,745 | 8/1969 | Fouche | 424/250 |
| 3,461,126 | 8/1969 | Fouche | 544/381 |
| 3,661,909 | 5/1972 | Mastursi et al. | 544/381 |
| 3,720,676 | 3/1973 | Schindler et al. | 544/381 |
| 3,786,095 | 1/1974 | Kyburz et al. | 544/381 |
| 3,917,602 | 11/1975 | Normant | 544/381 |
| 3,928,356 | 12/1975 | Umio et al. | 544/381 |

FOREIGN PATENT DOCUMENTS

| | | |
|---|---|---|
| 1000701 | 11/1976 | Canada . |
| 1568089 | 1/1970 | Fed. Rep. of Germany . |
| 1620151 | 7/1971 | Fed. Rep. of Germany . |
| 1129029 | 10/1968 | United Kingdom . |

OTHER PUBLICATIONS

J. Schmutz, Arzneim-Forsch (Drug Research) 25 (1975), pp. 712–720.

E. L. Engelhardt et al., J. Med. Chem. 8 (1965), pp. 829–835.

Primary Examiner—Mary C. Lee
Assistant Examiner—James H. Turnipseed
Attorney, Agent, or Firm—Keil & Witherspoon

[57] ABSTRACT

10-Substituted 5-cyanomethylene-10,11-dihydro-dibenzo[a,d]-cycloheptenes, their pharmaceutically tolerated addition salts with acids, processes for their preparation, and their use as drugs, especially as sedatives, hypnotics or tranquilizers.

10 Claims, No Drawings

10-SUBSTITUTED 5-CYANOMETHYLENE-10,11-DIHYDRO-DIBENZO-[A,D]-CYCLOHEPTENES, THEIR PREPARATION, AND THERAPEUTIC AGENTS CONTAINING THESE COMPOUNDS

The present invention relates to 10-substituted 5-cyanomethylene-10,11-dihydro-dibenzo[a,d]-cycloheptenes and their pharmaceutically tolerated addition salts with acids, processes for their preparation, and the use of the compounds as drugs, especially as sedatives, hypnotics or tranquilizers.

It is known that tricyclic ring systems with a dibenzo structure and a central heterocyclic 7-membered ring, which may or may not possess a basic branch, for example an N-methylpiperazine radical, can exhibit neuroleptic effects. Examples of such tricyclic compounds are N-methylpiperazine derivatives of dibenzo[b,e][1,4]-diazepines (clozapine), dibenzo[b,f][1,4]-thiazepines (clotiapine), dibenzo[b,f][1,4]-oxazepines (loxapine) or morphantridines (perlapine), as described, for example, in the review by J. Schmutz in Arzneimittelforschung 25 (1975), 712–720.

German Patent Application No. P 2,918,778.8 proposes 6-substituted 11-alkylene-morphantridines having valuable pharmacological properties. The application in question concerns derivatives having a modified ring system and exhibiting a different pattern of pharmacological effects.

We have found that 10-substituted 5-cyanomethylene-10,11-dihydro-dibenzo[a,d]-cycloheptenes of the general formula I

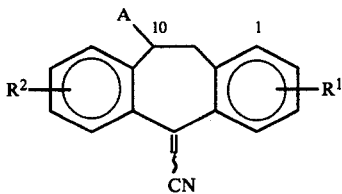

where $R^1$ and $R^2$ are hydrogen, halogen, especially fluorine, chlorine or bromine, alkyl of 1 to 3 carbon atoms or trifluoromethyl, and A is an amino radical $-NR^3R^4$, where $R^3$ and $R^4$ together with the nitrogen atom by which they are linked are a 5-, 6- or 7-membered saturated ring, which may or may not contain a nitrogen or an oxygen atom as a further hetero-atom, an additional nitrogen atom being unsubstituted or substituted by alkyl of 1 to 3 carbon atoms, hydroxyalkyl of 2 or 3 carbon atoms, alkoxyalkyl, the alkoxy and alkyl radical each being of 1 to 3 carbon atoms, cycloalkyl or cycloalkylmethyl, of 3 to 7 carbon atoms in the cycloalkyl ring, or alkynyl of 2 to 5 carbon atoms and being additionally, where appropriate, substituted by oxygen in the form of an N-oxide, and their physiologically tolerated addition salts with acids, exhibit valuable pharmacological properties.

Important meanings of $R^1$ and $R^2$ include hydrogen, fluorine, chlorine, methyl and trifluoromethyl, amongst which hydrogen and chlorine are particularly preferred.

Examples of amine radicals A, ie. $-NR^3R^4$, are piperazinyl, homopiperazinyl, piperidinyl and morpholinyl.

Particularly preferred radicals $-NR^3R^4$ are 4-methyl-piperazinyl, 4-methyl-4-oxy-piperazinyl, 4-cyclopropyl-piperazinyl, 4-cyclopropylmethyl-piperazinyl, 4-prop-2-ynyl-piperazinyl, 4-(2-hydroxy)-ethyl-piperazinyl, 4-ethyl-piperazinyl and N-methyl-homopiperazinyl.

It is to be noted that the novel compounds of the formula I exist as cis-trans isomers Ia and Ib.

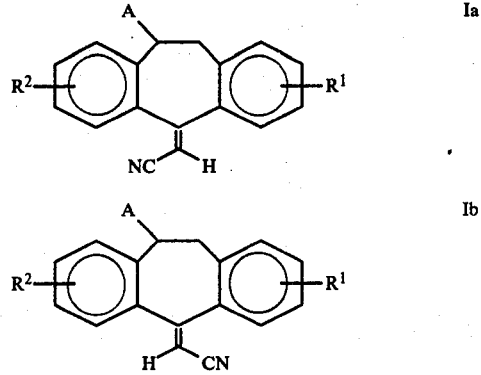

If desired, the cis-trans isomers (which are as a rule present in the form of 1:1 mixtures) can be separated, for example by fractional crystallization or by column chromatography.

In accordance with the above meanings, the following compounds may be mentioned as being particularly preferred and active: cis,trans-5-cyanomethylene-10-(4-methyl-piperazin-1-yl)-10,11-dihydro-dibenzo[a,d]-cycloheptene, cis,trans-5-cyanomethylene-10-(4-methyl-4-oxy-piperazin-1-yl)-10,11-dihydro-dibenzo[a,d]-cycloheptene, cis,trans-5-cyanomethylene-2-chloro-10-(4-methyl-piperazin-1-yl)-10,11-dihydro-dibenzo[a,d]-cycloheptene, cis,trans-5-cyanomethylene-10-(4-β-hydroxyethylpiperazin-1-yl)-10,11-dihydro-dibenzo[a,d]-cycloheptene, cis,trans-5-cyanomethylene-10-(4-ethyl-piperazin-1-yl)-10,11-dihydro-dibenzo[a,d]-cycloheptene and cis,trans-5-cyanomethylene-10-(N'-methyl-homopiperazin-1-yl)-10,11-dihydro-dibenzo[a,d]-cycloheptene.

The novel compounds of the formula I are prepared by reacting a compound of the formula II

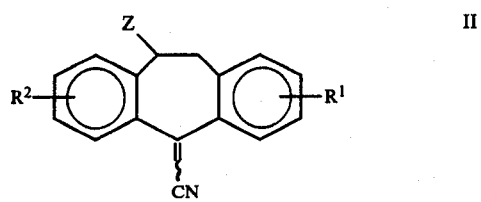

where $R^1$ and $R^2$ have the meanings given for formula I, or the preferred meanings, and Z is a nucleofugic leaving group, with a nucleophilic agent AH, where A has the meanings given for formula I, and, if desired, converting the resulting compound to the N-oxide and/or to an addition salt with a physiologically tolerated acid.

Suitable nucleofugic leaving groups Z are halogen, especially bromine and chlorine, preferably bromine.

The reaction is advantageously carried out in the presence of an excess of the amine AH, in a dipolar aprotic solvent, preferably dimethylformamide, in the presence of about ⅔ mole equivalent of a monovalent silver or copper salt, preferably of silver nitrate, at from room temperature to 80° C., and is in general complete within from 0.5 to 4 hours. In some cases, it may be advantageous to exclude atmospheric oxygen and carry out the reaction under an inert gas, for example under nitrogen.

In the reactions, the nucleophilic agent AH is advantageously used in not less than 2-molar, and up to 20-molar, excess.

Advantageously, the 5-cyanomethylene-dibenzo[a,d]-cycloheptene formed as a by-product in the reaction, through elimination of hydrogen halide, is separated off by column chromatography.

The conversion of a compound of the formula I to its N-oxide is carried out in a conventional manner, advantageously with aqueous (30% strength by weight) hydrogen peroxide in ethanol solution. The conversion of a compound to its addition salt with a physiologically tolerated acid is also carried out in a conventional manner.

The starting compounds of the formula II are prepared by reacting a 5-cyanomethylene-10,11-dihydrodibenzo[a,d]-cycloheptene of the formula III

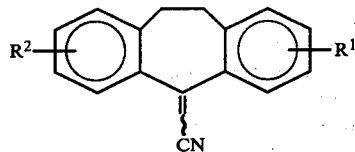

where $R^1$ and $R^2$ have the meanings given for formula I, with 1 mole of N-bromosuccinimide or N-chlorosuccinimide in a halohydrocarbon, at from 50° to 100° C., to give the 10-bromo-(chloro)-5-cyanomethylene-10,11-dihydro-dibenzo[a,d]-cycloheptene of the formula II.

The 5-cyanomethylene-10,11-dihydro-dibenzo[a,d]-cycloheptenes of the formula III are prepared by a carbonyl olefination, wherein a dibenzosuberone (known from the literature) of the formula IV (cf. E. L. Engelhardt et al., J. Med. Chem. 8 (1965) 829)

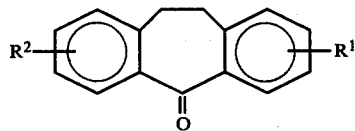

wherein $R^1$ and $R^2$ have the meanings given for formula I, is reacted with a phosphonate of the formula IVa

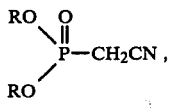

where R is alkyl of 1 to 3 carbon atoms, under the conditions of a Wittig-Horner reaction, in an inert solvent-dimethylformamide being particularly preferred—in the presence of one mole equivalent of a base, preferably a sodium alcoholate, sodium hydride or sodium amide, at from 20° to 80° C., or is reacted with a phosphonium salt of the formula IVb

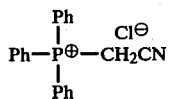

where Ph is a phenyl radical, under the conditions of a classical Wittig reaction, in an aprotic organic solvent, especially a saturated aliphatic or saturated cyclic ether, eg. diethyl ether, tetrahydrofuran or dioxane, or, preferably, in dimethylformamide, in the presence of one mole equivalent of a base, especially of an alkali metal alcoholate, preferably sodium methylate or sodium ethylate, or sodium hydride or sodium amide, or of an organometallic compound, such as butyl-lithium, at from 20° to 100° C.

In addition to the compounds referred to in the Examples, the following compounds may be mentioned by way of illustration: cis,-trans-8-chloro-5-cyanomethylene-10-(4-methyl-piperazin-1-yl)-10,11-dihydro-dibenzo-[a,d]-cycloheptene, cis,trans-5-cyanomethylene-10-(4-cyclopropyl-piperazin-1-yl)-10,11-dihydro-dibenzo[a,d]-cycloheptene, cis,trans-5-cyanomethylene-10-(4-cyclopropylmethyl-piperazin-1-yl)-10,11-dihydro-dibenzo[a,d]-cycloheptene and cis,trans-5-cyanomethylene-10-(4-prop-2-ynyl-piperazin-1-yl)-10,11-dihydro-dibenzo[a,d]-cycloheptene.

The compounds according to the invention, of the formula I, are as a rule obtained in the form of yellowish or yellow crystals, and can be recrystallized from the conventional organic solvents, preferably from a lower alcohol, such as ethanol, or be purified by column chromatography.

The free 10-substituted 5-cyanomethylene-10,11-dihydro-dibenzo[a,d]-cycloheptenes of the formula I can be converted to an addition salt with a pharmacologically tolerated acid in a conventional manner, preferably by adding one equivalent of the corresponding acid to the solution. Examples of suitable conventional physiologically tolerated acids are, amongst inorganic acids, hydrochloric acid, hydrobromic acid, phosphoric acid and sulfuric acid, and, amongst organic acids, oxalic acid, maleic acid, fumaric acid, lactic acid, tartaric acid, malic acid, citric acid, salicylic acid, adipic acid and benzoic acid; other acids are listed in Fortschritte der Arzneimittelforschung, published by Birkhäuser, Basel and Stuttgart, 10 (1966), 224–225.

The compounds according to the invention possess valuable pharmacological properties. They may be used as sedatives, tranquilizers, hypnotics, neuroleptics or antidepressants. Any one compound according to the invention may exhibit one or more of the above types of effect.

According to the results of the pharmacological experiments we have carried out, the compounds according to the invention are, by virtue of their sedative-tranquilizing, muscle-relaxing and anti-monaminergic effect, particularly suitable for use as sedatives, hypnotics and minor or major tranquilizers.

The following methods were used to analyze the action of the compounds:

1. Sedative action

4–8 groups of 3 female NMRI mice are given the compound orally. The orientation hypermotility induced by a new environment is determined photoelectrically, 30 minutes after administration of the compound, for a period of 30 minutes.

The $ED_{50}$ is the dose which produces a decrease in orientation hypermotility by 50%, compared to control animals treated with placebo.

2. Muscle-relaxing action

The measurement is based on quantifying the tonic extensor reflex on the rabbit gastrocnemius (Teschendorf et al., Arch. Pharmacol. exp. Path. 266 (1970), 462). The rabbit is fixed in a special apparatus which permits bending the paw at the talocalcanean joint in a defined and reproducible manner. As a result of this bending, a tonic extensor reflex is triggered in the thigh muscle. The electrical activity of the muscle during contraction is registered and the individual pulses are counted. The extension (duration 5 s) is repeated at intervals of one minute. After a constant number of pulses has been reached (constituting the control value), the test compound is administered intravenously. The number of pulses after administration is related to the previous value. For each dose investigated, 4–6 animals are used. The ED 50% is the dose which reduces the muscle activity to half, based on the initial value.

3. Antimethamphetamine action

Methamphetamine (2.5 mg/kg administered intravenously) regularly causes the following symptoms in rats: motor restlessness, searching and sniffing movements, bristling fur and tremor (Janssen et al., Arzneim.-Forsch./Drug Res. 13 (1963), 205; Randrug et al., Psychopharmacologia 11 (1967), 300). The test substances are administered intraperitoneally, 30 minutes before the methamphetamine. The criterion of whether a compound has an effect is whether the sniffing movements remain absent over 5 minutes' observation after the injection of methamphetamine. That dose is determined as the mean inhibitory dose (ED 50%) by means of Probit analysis which prevents the symptom in half the number of animals. Number of animals examined per dose: 10.

4. Antiapomorphine action

Mandibular movements are triggered in groups of 4–6 female Sprague-Dawley rats by subcutaneous administration of 1.5 mg/kg of apomorphine and are registered by implanted electrodes (mandibulogram as described by Kubacki, Psychopharmacology 59 (1978), 209). The test substances are administered orally 90 minutes before the apomorphine.

The ED 50% is determined as the dose which reduces the number of mandibular movements by 50% compared to those in placebo-treated control animals.

5. Anticholinergic action

Groups of 10 female NMRI mice are given physostigmine subcutaneously, at a lethal dose (0.825 mg/kg). The test substances are administered orally 30 minutes before the administration of physostigmine.

The ED 50% is determined as the dose of compound which protects 50% of the animals against death from physostigmine.

6. Acute toxicity

Groups of 5–10 female NMRI mice are given the compounds intraperitoneally. The LD 50 is determined as the dose after which 50% of the treated animals die.

In these experiments (cf. Table 1) conspicuously sedative-hypnotic effects of the compounds according to the invention were demonstrated, these effects being about as pronounced as in the case of the reference compounds clozapine and perlapine. There is also a muscle-relaxing action, which in some cases markedly surpasses those of the comparative substances; this is the case with the compounds of Example 4.

The antimonaminergic action, measured in the present case in terms of the methamphetamine-antagonism or apomorphine-antagonism, may be regarded as a parameter of the neuroleptic quality. The strength of the effect is as great as or even markedly (up to 7 times) greater than in the case of the comparative compounds clozapine and perlapine. In contrast to clozapine, the novel compounds show no anticholinergic properties, as demonstrated by the antiphysostiamine test on mice, from which it may be concluded that the peripheral side-effects on therapeutic use are less.

On the basis of the pharmacological findings, the novel compounds can be used, in appropriate pharmaceutical formulations, as sedatives, hypnotics, minor tranquilizers or major tranquilizers.

TABLE 1

| Example No. | Sedation ED 50% | Sedation R.A.[1] | Muscle relaxation ED 50% | Muscle relaxation R.A. | Antimethamphetamine action ED 50% | Antimethamphetamine action R.A. | Antiapomorphine action ED 50% | Antiapomorphine action R.A. | Anticholinergic action LD 50 | Toxicity LD 50 |
|---|---|---|---|---|---|---|---|---|---|---|
| 1 | 5.6 | 0.85 | 0.1 | 0.46 | 5.4 | 6.85 | | | >46.4 | >100 |
| 7 | 10.0 | 0.47 | | | 30 | 1.23 | | | >100 | >100 |
| 5 | 6.7 | 0.71 | 0.1 | 0.46 | 13 | 2.85 | | | >46.4 | >100 |
| 8 | 15.2 | 0.31 | | | 39 | 0.95 | 7 | 1.14 | >100 | >100 |
| 4 | 5.5 | 0.86 | 0.02 | 2.30 | 4.6 | 8.04 | | | | |
| Clozapine | 4.74 | 1.0 | 0.046 | 1.0 | 37 | 1.00 | 8 | 1.00 | 14.1 | 215 |
| Perlapine | 2.01 | 2.36 | 0.1 | 0.46 | 31 | 1.19 | 21.5 | 0.37 | >21.5 | 215 |

[1]R.A. = relative activity

Accordingly, the present invention also relates to a therapeutic agent which in addition to conventional carriers and diluents contains a compound of the formula I, or a physiologically tolerated addition salt thereof with an acid, as the active compound.

Therapeutic agents containing conventional carriers or diluents and the conventionally used technical auxiliaries can be prepared in a conventional manner, in accordance with the desired route of administration and employing a unit dosage suitable for the particular application. A suitable individual dose in man is from 10 to 100 mg.

The novel compounds may be employed in the conventional solid or liquid pharmaceutical forms, such as tablets, capsules, powders, granules, dragees or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, dragees, capsules, pills, powders, solutions, suspensions and depot forms. Parenteral formulations, such as injection solutions, may also be used. Suppositories are a further example of suitable formulations.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Accordingly, dragees can be prepared by coating cores, prepared similarly to the tablets, with agents conventionally used in dragee coatings, for example collidone or shellac, gum arabic, talc, titanium dioxide or sugar. The dragee coating can also consist of a plurality of layers, and the auxiliaries mentioned above in connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The Examples which follow illustrate the invention.

EXAMPLE 1 cis,trans-5-Cyanomethylene-10-(4-methyl-piperazin-1-yl)-10,11-dihydro-dibenzo[a,d]-cycloheptene. ½ H$_2$O 1.0 g (5.9 millimoles) of silver nitrate are dissolved in 10 ml of stirred absolute dimethylformamide, and a large excess (5–50 ml) of N-methylpiperazine is added. A solution of 7.0 g (22.6 millimoles) of 10-bromo-5-cyanomethylene-10,11-dihydro-dibenzo[a,d]-cycloheptene (cis,trans-isomer mixture) in 35 ml of dimethylformamide is then immediately added dropwise (a slight rise in temperature of the reaction mixture, to 28°–30° C., indicates the exothermic reaction is taking place, and the color changes from yellow to gray as a result of precipitated silver), and the reaction mixture is stirred for 1–3 hours at room temperature, under nitrogen. It is then poured onto 2 liters of ice water (thorough stirring being necessary), and after a further hour's stirring the gray solids which have precipitated are filtered off. The crude product, which is colored gray due to finely divided silver, is dispersed in a small amount of methylene chloride and is purified direct by column chromatography on silica gel, using a 95/5 methylene chloride/methanol mixture; this removes the 5-cyanomethylene-dibenzo[a,d]-cycloheptene formed as a by-product. 1.5 g (20%) of product are isolated as a cis,trans-isomer mixture, which can subsequently be recrystallized from ethanol. Colorless crystals of melting point 141°–143° C.

EXAMPLE 2 cis,trans-10-Bromo-5-cyanomethylene-10,11-dihydro-dibenzo[a,d]-cycloheptene

To prepare the intermediate 10-bromo-5-cyanomethylene-10,11-dihydro-dibenzo[a,d]-cycloheptene, 13.0 g (56 millimoles) of 5-cyanomethylene-10,11-dihydro-dibenzo[a,d]-cycloheptene are dissolved in 200 ml of carbon tetrachloride and 10.0 g (56 millimoles) of N-bromosuccinimide and 100 mg of benzoyl peroxide are added. The reaction mixture is refluxed for 3 hours and when it has cooled the succinimide formed is filtered off. After concentrating the mother liquor, the crude product is obtained as a crystal/oil mixture, which is recrystallized from ethanol. 16.0 g (92%) of product of melting point 148°–150° C. are isolated.

EXAMPLE 3 cis,trans-5-Cyanomethylene-10,11-dihydro-dibenzo[a,d]-cycloheptene

To prepare the intermediate 5-cyanomethylene-10,11-dihydro-dibenzo[a,d]-cycloheptene, a carbonyl olefination is carried out by means of a Wittig-Horner reaction or by a classical Wittig synthesis: 20.0 g (96 millimoles) of dibenzosuberone are dissolved in 200 ml of warm dimethylformamide and the solution is stirred under nitrogen. 20.3 g (115 millimoles) of diethyl-cyanomethyl-phosphonate and 20.1 g (115 millimoles) of 30% strength sodium methylate dissolved in 100 ml of dimethylformamide are then slowly and simultaneously added dropwise (an intensification of color, and rise in temperature, indicate the start of the Wittig reaction). After stirring for a further 12 hours at room temperature, the reaction product is poured onto ice water and stirred thoroughly for 3 hours to complete the crystallization, and the solid which has precipitated is filtered off. After thorough washing with water, the crude product is dried and recrystallized from ethanol. Yield: 14.0 g (63%) of colorless crystals of melting point 105°–107° C.

Classical Wittig process: Triphenyl-cyanomethyl-phosphonium chloride is introduced into dimethylformamide, 1 mole equivalent of a 30% strength sodium methylate solution is then added dropwise, or 1 mole equivalent of sodium hydride is added, and finally 1 mole equivalent of a solution of dibenzosuberone in dimethylformamide is introduced. The reaction mixture is stirred for 5–8 hours at 50°–80° C. and is then poured onto ice water and extracted repeatedly with methylene chloride. The organic phase is dried and concentrated, and the crude product obtained is recrystallized from ethanol. Yield: 45%; colorless crystals of melting point 104°–107° C.

EXAMPLE 4 cis,trans-2-Chloro-5-cyanomethylene-10-(4-methylpiperazin-1-yl)-10,11-dihydro-dibenzo[a,d]-cycloheptene (a) cis,trans-2-Chloro-5-cyanomethylene-10,11-dihydro-dibenzo[a,d]-cycloheptene The synthesis is carried out analogously to Example 3, with different working up by extracting the crude product from ice water with methylene chloride, followed by washing the organic phase three times with water and drying and concentrating it.

The cis,trans-isomer mixture obtained as a crystal/oil mixture is subjected to fractional crystallization from ethanol, the most sparingly soluble fraction is isolated, and this operation is repeated two or three times, in each case with the most sparingly soluble fraction, to give the pure trans-isomer, of melting point 142°–143° C. (analysis by 270 MHz $^1$H-NMR spectroscopy in CDCl$_3$: the doublet of H$_6$ which appears in the lowest field, of $\delta$=7.45 ppm, exhibits m-coupling, which naturally does not occur with the cis-isomer).

(b) cis,trans-10-Bromo-2-chloro-5-cyanomethylene-10,11-dihydro-dibenzo[a,d]-cycloheptene: Synthesis similar to Example 2. Colorless crystals of melting point 142°–145° C. (after recrystallization from ethanol).

(c) cis,trans-2-Chloro-5-cyanomethylene-10-(4-methyl-piperazin-1-yl)-10,11-dihydro-dibenzo[a,d]-cycloheptene: Synthesis similar to Example 1. After column chromatography (silica gel, 95/5 methylene chloride/methanol), colorless crystals of melting point 77°–80° C. are obtained.

EXAMPLE 5 cis,trans-5-Cyanomethylene-10-(4-ethyl-piperazin-1-yl)-10,11-dihydro-dibenzo[a,d]-cycloheptene. ½ H$_2$O Synthesis similar to Example 1, using N-ethylpiperazine. After purification by column chromatography (silica gel, 95/5 methylene chloride/methanol), colorless crystals of melting point 68°–71° C. are obtained.

EXAMPLE 6 cis,trans-5-Cyanomethylene-10-(N′-methyl-homopiperazin-1-yl)-10,11-dihydro-dibenzo[a,d]-cycloheptene. ½ H$_2$O Synthesis similar to Example 1, using N-methyl-homopiperazine. After purification by column chromatography (silica gel, 95/5 methylene chloride/methanol), colorless crystals of melting point 85°–88° C. are obtained.

EXAMPLE 7 cis,trans-5-Cyanomethylene-10-(N-$\beta$-hydroxyethyl-piperazin-1-yl)-10,11-dihydro-dibenzo[a,d]-cycloheptene. ½ H$_2$O Synthesis similar to Example 1, using N-$\beta$-hydroxyethyl-piperazine. After purification by column chromatography (silica gel, 95/5 methylene chloride/methanol), colorless crystals of melting point 75°–78° C. are obtained.

EXAMPLE 8 cis,trans-5-Cyanomethylene-10-(4-methyl-4-oxy-piperazin-1-yl)-10,11-dihydro-dibenzo[a,d]-cycloheptene. ½ H$_2$O 2.4 g (7.3 milimoles) of cis,trans-5-cyanomethylene-10-(4-methyl-piperazin-1-yl)-10,11-dihydro-dibenzo[a,d]-cycloheptene (Example 1) are dissolved in 100 ml of hot ethanol and 5 ml of 30% strength hydrogen peroxide are added. After refluxing the mixture for 5 hours, the excess hydrogen peroxide is destroyed by dropping a small platinum sheet into the reaction mixture and then refluxing for 2 hours. After filtration, the reaction mixture is concentrated and the N-oxide obtained is purified by column chromatography (silica gel, mobile phase 95/5 methylene chloride/methanol). 1.5 g (60%) of colorless crystals of melting point 78°–80° C. are isolated.

Pharmaceutical formulations prepared in a conventional manner:

| Examples of tablets | |
|---|---|
| 1. An active compound of the formula I | 5 mg |
| Lactose | 200 mg |
| Methylcellulose | 15 mg |
| Corn starch | 50 mg |
| Talc | 11 mg |
| Magnesium stearate | 4 mg |
| 2. An active compound of the formula I | 20 mg |
| Lactose | 178 mg |
| Avicel | 80 mg |
| Polywachs 6000 | 20 mg |
| Magnesium stearate | 2 mg |
| 3. An active compound of the formula I | 50 mg |
| Polyvinylpyrrolidone (mean molecular weight 25,000) | 170 mg |
| Polyethylene glycol (mean molecular weight 4,000 | 14 mg |
| Hydroxypropylmethylcellulose | 40 mg |
| Talc | 4 mg |
| Magnesium stearate | 2 mg |

The active compound is moistened with a 10% strength aqueous solution of the polyvinylpyrrolidone and the mixture is forced through a sieve of 1.0 mm mesh width and is dried at 50° C. The granules thus obtained are mixed with polyethylene glycol (mean molecular weight 4,000), hydroxypropylmethylcellulose, talc and magnesium stearate and the mixture is pressed to give tablets each weighing 280 mg.

| 4. Example of dragees | |
|---|---|
| An active compound of the formula I | 60 mg |
| Lactose | 90 mg |
| Corn starch | 60 mg |
| Polyvinylpyrrolidone | 6 mg |
| Magnesium stearate | 1 mg |

The mixture of the active compound with lactose and corn starch is moistened with an 8% strength aqueous solution of the polyvinylpyrrolidone and granulated by passing through a 1.5 mm sieve; the granules are dried at 50° C. and forced through a 1.0 sieve. The granules obtained after this operation are mixed with magnesium stearate and the mixture is pressed to form dragee cores. These are coated in a conventional manner with a shell which essentially consists of sugar and talc.

| 5. Capsule formulation | |
|---|---|
| An active compound of the formula I | 5 mg |
| Magnesium stearate | 2.0 mg |
| Lactose | 19.3 mg |
| 6. Injection solution | |
| An active compound of the formula I | 10 mg |
| Sodium chloride | 9 mg |
| Distilled water, q.s. to make 1.0 ml | |

We claim:

1. A 10-substituted 5-cyanomethylene-10,11-dihydro-dibenzo[a,d]-cyclopheptene of the formula I

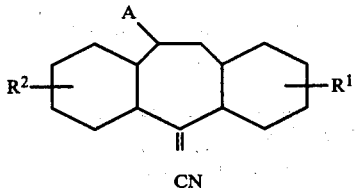

where R[1] and R[2] are hydrogen, halogen, alkyl of 1 to 3 carbon atoms or trifluoromethyl, and A is piperazinyl, homopiperazinyl, piperidinyl or morpholinyl, an additional nitrogen atom being unsubstituted or substituted by alkyl of 1 to 3 carbon atoms, hydroxyalkyl of 2 or 3 carbon atoms, alkoxyalkyl, the alkoxy and alkyl radical each being of 1 to 3 carbon atoms, cycloalkyl or cycloalkylmethyl, of 3 to 7 carbon atoms in the cycloalkyl ring, or alkynyl of 2 to 5 carbon atoms and being additionally, where appropriate, substituted by oxygen in the form of an N-oxide, and its physiologically tolerated addition salts with acids.

2. A compound of the formula I as defined in claim 1, where R[1] and R[2] are hydrogen or chlorine and A is a piperazine or homopiperazine radical which is substituted at the ring nitrogen by methyl, ethyl, β-hydroxyethyl, cyclopropyl or propynyl and which may or may not be in the form of the N-oxide.

3. A compound of the formula I as claimed in claim 1, where R[1] and R[2] are hydrogen or chlorine and A is 4-methyl-piperazin-1-yl, 4-β-hydroxyethyl-piperazin-1-yl, 4-ethyl-piperazin-1-yl, 4-methyl-4-oxy-piperazin-1-yl or N'-methyl-homopiperazin-1-yl.

4. cis,trans-5-Cyanomethylene-10-(4-methyl-piperazin-1-yl)-10,11-dihydro-dibenzo[a,d]-cycloheptene.

5. cis,trans-5-Cyanomethylene-10-(4-methyl-4-oxypiperazin-1-yl)-10,11-dihydro-dibenzo[a,d]-cycloheptene.

6. cis,trans-5-Cyanomethylene-10-(4-β-hydroxyethyl-piperazin-1-yl)-10,11-dihydro-dibenzo[a,d]-cycloheptene.

7. cis,trans-5-Cyanomethylene-10-(4-ethyl-piperazin-1-yl)-10,11-dihydro-dibenzo[a,d]-cycloheptene.

8. cis,trans-5-Cyanomethylene-2-chloro-10-(4-methyl-piperazin-1-yl)-10,11-dihydro-dibenzo[a,d]-cycloheptene.

9. cis,trans-5-Cyanomethylene-10-(N'-methyl-homopiperazin-1-yl)-10,11-dihydro-dibenzo[a,d]-cycloheptene.

10. A therapeutic sedative, hypnotic or tranquilizing agent, which contains a therapeutically effective amount of a compound of the formula I as defined in claim 1, or a pharmacologically tolerated acid addition salt thereof, as the active compound, together with conventional carriers and diluents.

* * * * *

UNITED STATES PATENT AND TRADEMARK OFFICE
CERTIFICATE OF CORRECTION

PATENT NO. : 4,376,773
DATED : March 15, 1983
INVENTOR(S) : Gerd STEINER et al.

It is certified that error appears in the above-identified patent and that said Letters Patent is hereby corrected as shown below:

IN THE TITLE:

Change "A,D" to --a,d--.

Claim 1, add circles to phenyl rings.

Signed and Sealed this

Third Day of January 1984

[SEAL]

Attest:

GERALD J. MOSSINGHOFF

Attesting Officer   Commissioner of Patents and Trademarks